United States Patent [19]

Kametaka et al.

[11] 4,278,820

[45] Jul. 14, 1981

[54] PROCESS FOR PREPARING MONOALKYLENE GLYCOL MONOETHERS

[75] Inventors: Norio Kametaka, Hiratsuka; Kuniomi Marumo; Tutomu Nozawa, both of Tokyo, all of Japan

[73] Assignee: Showa Denka K.K., Tokyo, Japan

[21] Appl. No.: 81,619

[22] Filed: Oct. 3, 1979

[30] Foreign Application Priority Data

Oct. 5, 1978 [JP] Japan ................................. 53/121979

[51] Int. Cl.³ ............................................. C07C 41/03
[52] U.S. Cl. .................................. 568/678; 568/679; 568/678; 252/455 R; 252/458; 252/959; 252/449
[58] Field of Search ................ 568/678, 679, 680, 618

[56] References Cited

U.S. PATENT DOCUMENTS

| | | |
|---|---|---|
| 1,996,003 | 3/1935 | Dehnert et al. . |
| 3,328,467 | 6/1967 | Hamiton ............................... 568/618 |

FOREIGN PATENT DOCUMENTS

| | | | |
|---|---|---|---|
| 555463 | 7/1932 | Fed. Rep. of Germany | ........... 568/678 |
| 558646 | 9/1932 | Fed. Rep. of Germany | ........... 568/678 |
| 1481895 | 8/1977 | United Kingdom | ..................... 568/678 |

OTHER PUBLICATIONS

C & EN Aug. 23, 1976 p. 26.

*Primary Examiner*—Howard T. Mars
*Attorney, Agent, or Firm*—Wenderoth, Lind & Ponack

[57] ABSTRACT

A monoalkylene glycol monoether is produced with good efficiency and commercial advantage by reacting an alkylene oxide with an alcohol in the presence of a solid catalyst resulting from the exchange of exchangeable cations of a montmorillonite clay with a cation of Al, Cr, Mn, Fe, Sn or Th.

6 Claims, No Drawings

PROCESS FOR PREPARING MONOALKYLENE GLYCOL MONOETHERS

This invention relates to a process for producing a monoalkylene glycol monoether by reacting an alkylene oxide with an alcohol, and specifically, to a process for producing the desired monoalkylene glycol monoether in good yields with commercial advantage by performing the aforesaid reaction in the presence of an improved catalyst.

Monoalkylene glycol monoethers are useful as water-soluble high-boiling solvents or industrial intermediates for various compounds, and are known to be produced by reacting alkylene oxides, for example alkylene oxides having 2 to 4 carbon atoms such as ethylene oxide, propylene oxide and butylene oxide, with aliphatic lower alcohols, for example aliphatic alcohols having 1 to 4 carbon atoms such as methanol, ethanol, propanol and butanol in the liquid phase in the presence of an acid or basic catalyst. The monoalkylene glycol monoethers can also be produced in the absence of a catalyst. But, since the rate of the reaction is low, very high temperatures and pressures are required. It is known that mineral acids such as sulfuric acid and phosphoric acid, and Lewis acids such as boron trifluoride and aluminum chloride can be effectively used as the acid catalysts; and alkali metal hydroxides, alkoxides and alkylamines are effective as the basic catalysts. However, since these catalysts uniformly dissolve in the reaction system, they pose engineering problems such as the separation of the catalyst from the reaction product, its post-treatment and its recycling, or the corrosion of the reaction apparatus. Accordingly, various solid acids and solid bases including zeolite, ion exchange resins and activated clay have been suggested as commercial catalysts free from such problems.

In the reaction of an alkylene oxide with an alcohol, fairly large amounts of by-products such as a dialkylene glycol ether or a trialkylene glycol ether form in addition to the desired monoalkylene glycol monoether, and reduce the yield of the desired product. The conventional catalysts have their own advantages and disadvantages in commercial production. For example, those having a relatively high activity are inferior in selectivity for the desired product. Alternatively, those which show good selectivity have low activity. Even those which show satisfactory activity and selectivity may undergo deterioration or vary in performance within relatively short periods of time, and are difficult to use stably over a long period of time.

The present inventors have made various investigations in order to develop catalysts which have high activity, and good selectivity for the desired product and which can retain their high performance stably over a long period of time in the liquid-phase reaction of an alkylene oxide with an alcohol to produce an alkylene glycol monoether. These investigations have led to the discovery that this object can be achieved by using a solid catalyst resulting from the exchanging of exchangeable cations of a clay composed mainly of montmorillonite typified by acid clays and bentonite with at least one cation selected from the group consisting of aluminum, chromium, manganese, iron, tin and thorium cations.

It has previously been known to use an acid clay or activated clay in a method for preparing an alkylene glycol monoether by reacting an alkylene oxide with an alcohol. However, the acid clay does not have sufficient activity and selectivity for use in this reaction, and the activated clay has only a slightly higher activity than acid clay.

Acid clay derived its name from the fact that when it is filtered upon the addition of an aqueous solution of a neutral salt such as potassium chloride, hydrochloric acid is found in the filtrate. The acid clay is a typical example of clays having montmorillonite as a main ingredient. A group of the acid clay includes Japanese acid clay occurring in Japan, fuller's earth occurring in Britain, Warker-erde and Bleich-erde occurring in Germany and Florida earth occurring in U.S.A. The activated clay is a clay having enhanced adsorptive characteristics obtained by treating the acid clay with a mineral acid. The activated clay scarcely contains montmorillonite because the montmorillonite structure is broken in the process of acid treatment. Another typical example of the clay having montmorillonite as a main ingredient is bentonite which, however, does not belong to the acid clay. The montmorillonite contains an exchangeable cation such as an alkali metal or alkaline earth metal. It is known that these cations can be easily exchanged with other metal cations. The cation exchangeable capacity is about 50 meq./100 g for Japanese acid clay, and about 60 to 100 meq./100 g for bentonite.

It has now been found that a solid catalyst resulting from the exchanging of exchangeable cations in a clay having montmorillonite as a main ingredient with at least one metal cation selected from the group consisting of aluminum, chromium, manganese, iron, tin and thorium exhibits a markedly increased catalyst activity over the original clay not subjected to cation exchange in the production of an alkylene glycol monoether by the liquid-phase reaction of an alkylene oxide with an alcohol. It has also been found that in addition to the increase of catalytic activity, the solid catalyst provides a markedly improved selectivity for the monoalkylene glycol monoether. Thus, since the catalyst of this invention has a high activity and the materials at high flowing rates can be reacted with good efficiency with a high selectivity, the desired product can be produced in an increased space time yield (kg/liter of catalyst/hour).

The present invention is described in more detail below.

Not only acid clays and bentonite, but also any other clays having a montmorillonite content of at least 50% can be used as the clay which is the basis for obtaining the solid catalyst by exchanging with a specified metal cation.

There is no particular restriction on the method of preparing the solid catalyst used in this invention. Conveniently, the desired solid catalyst can be easily prepared in the following manner. Since, as described hereinabove, montmorillonite contains a cation of an alkali metal or an alkaline earth metal which can be easily exchanged with another metal cation, treatment of a montmorillonite-containing clay with an aqueous solution of a water-soluble salt of the specified metal can readily effect the desired cation exchange. The treatment can be performed by suitable methods such as suspension stirring treatment and flowing treatment. The suspension stirring treatment which comprises putting a powder of the clay into an aqueous solution of the salt of the specified metal and stirring the mixture is convenient. The size of the powder is preferably of approximately 100 mesh under. Room temperature sufices as the treating temperature, but if desired, an elevated temperature may be used. The amount of the metal salt used is that which corresponds to the cation exchanging capacity of the clay, and is usually 1 meq. (milliequivalents) or more/g of clay. The suitable concentration of the clay in the treating solution is 10 to 20% by weight. In this way, cation exchange can be easily performed. The extent of exchanging, if desired, can be known by determining the amount of the metal salt remaining in the treating solution. Suitable metal salts are water-soluble salts such as chlorides, sulfates, nitrates and acetates.

The clay powder treated with an aqueous solution of the metal salt is filtered and repeatedly washed with water to remove the adhering excess metal salt, and then dried at a temperature of about 100° to 120° C. When the resulting catalyst is to be used in the form of a powder, it is then adjusted to the desired particle size. When the resulting product is to be used as a fixed bed catalyst, a binder such as silica sol or alumina sol is added to the dried powder, and the mixture is molded into the desired size, dried and then calcined at a temperature of about 300° to 600° C.

The type of reaction to be performed in the presence of the solid catalyst of this invention described above for the production of the monoalkylene glycol monoether may be any of a batchwise method in a stirring tank, a continuous method in a stirring tank, a flowing method using a fixed bed, and a flowing method using a fluidized bed. The flowing method using a fixed bed, however, is most preferred in order to take advantage of the very high activity of the solid catalyst in accordance with this invention, which shortens the time during which the solid catalyst is contacted with the reaction solution.

The reaction temperature is 30° to 200° C., preferably 50° to 150° C. The pressure varies depending upon the reaction temperature and the starting materials used, but is that which is sufficient to maintain the reaction mixture in the liquid state.

The mole ratio of the starting alcohol to the starting alkylene oxide can be varied widely. If the proportion of the alcohol is made higher, the selectivity for the desired monoether increases. However, in view of the cost of purification, the range of this mole ratio will naturally be limited. The suitable mole ratio of the alcohol to the alkylene oxide is from 2 to 20, preferably from 4 to 10.

In the flowing method, the liquid hourly space velocity (LHSV, or simply SV), i.e. the amount of the starting material mixture/the amount of the catalyst (liter/liter of catalyst/hour), can be maintained at a considerably high value because the catalyst in accordance with this invention has high activity. The suitable SV is 5 to 100, preferably 10 to 50. If the SV is increased, the space time yield of the desired product increases, but the selectivity for the product somewhat decreases.

Under the aforesaid reaction conditions, an alkylene oxide conversion of 100% can be obtained.

The following Examples and Comparative Examples illustrate the present invention and its advantages more specifically.

The acid clays and bentonite used to prepare catalysts in these Examples, and acid clays and activated clays used as catalysts in the Comparative Examples are shown below.

Acid clays

A: Commercially available product occurring in Yamagata Prefecture, Japan. It was used in Examples 1 to 8 and 10 to 21 after cation exchange. In Comparative Example 1, it was used without cation exchange.

B, C, D: Commercially available products occurring in Niigata Prefecture, Japan, They were used without cation exchange in Comparative Examples 2, 3 and 4.

Activated clays

E, F, G: Commercially available products. They were used in Comparative Examples 5, 6 and 7. In Comparative Example 8, the activated clay G was used after treatment with an aqueous solution of aluminum chloride.

Bentonite

H: Commercially available product occurring in Gunma Prefecture, Japan. It was used in Example 9 after cation exchange.

These clays were analyzed, and the results (% by weight) are tabulated below.

| | $SiO_2$ | $Al_2O_3$ | $Fe_2O_3$ | MgO | $TiO_2$ | CaO | $K_2O$ | $Na_2O$ | Heat ignition loss |
|---|---|---|---|---|---|---|---|---|---|
| A | 81.2 | 11.9 | 1.6 | 1.4 | 0.2 | 0.6 | 0.5 | | 15.3 |
| B | 78.4 | 14.2 | 3.3 | 3.4 | 0.2 | 0.8 | 0.6 | | 11.0 |
| C | 75.3 | 14.5 | 0.9 | 3.0 | 0.1 | 1.8 | 1.0 | | 14.7 |
| D | 71.2 | 14.7 | 2.9 | 2.3 | | 0.7 | 2.2 | | |
| E | 83.3 | 9.2 | 1.6 | 2.0 | 0.2 | 0.7 | 1.0 | | 5.3 |
| F | 79.1 | 10.8 | 1.3 | 0.9 | 0.2 | 0.8 | 1.7 | | 17.3 |
| G | 80.1 | 12.5 | 1.5 | 2.1 | | 0.7 | | | 7.1 |
| H | 77.3 | 13.5 | | 2.0 | | 1.0 | 0.3 | 2.90 | 3.8 |

EXAMPLE 1

Twenty grams of a powder of acid clay (A) was put into a solution of 1.61 g of $AlCl_3.6H_2O$ in 100 ml of water, and the mixture was stirred at room temperature for 1 hour, followed by filtration and water washing. The treated clay was mixed with colloidal silica in an amount of 20% by weight as $SiO_2$. The mixture was molded, dried at 120° C. for 5 hours, and calcined in a muffle furnace at 500° C. for 2 hours to afford a catalyst having a size of 0.5 to 1.0 mm.

Ten milliliters of the resulting catalyst was packed into a reaction tube having an inside diameter of 10 mm, and ethanol and ethylene oxide in a mole ratio of 10:1 which had been preheated to 90° C. were fed under a pressure of 10 $kg/cm^2.G$ at a speed of 200 ml/hour. The resulting solution was analyzed by gas-chromatography. It was found that the conversion of ethylene oxide was 100%, the selectivity for ethylene glycol monoethyl ether was 92.4%, and the selectivity for diethylene glycol monoethyl ether was 5.8%. Accordingly, the space time yield of the ethylene glycol monoethyl ether corresponded to 2.64 kg/liter of catalyst/hour.

From a comparison of this result with the result of Comparative Example 1 given hereinbelow which was operated under the same conditions as above except that the acid clay (A) was not treated with the aqueous aluminum chloride solution, it will be readily understood that the effect of this invention is very remarkable.

EXAMPLES 2 TO 8

Example 1 was repeated under the same conditions as in Example 1 except that the mole ratio of ethanol to ethylene oxide and the space velocity were varied. The results together with that obtained in Example 1 are summarized in Table 1. The selectivity and space time yield (STY) are those of ethylene glycol monoethyl ether.

TABLE 1

| Example | Mole ratio | SV | Conversion (%) | Selectivity (%) | STY (kg/l.cat./hr.) |
|---|---|---|---|---|---|
| 1 | 10 | 20 | 100 | 92.4 | 2.64 |
| 2 | 10 | 50 | 100 | 89.3 | 6.38 |
| 3 | 7 | 20 | 100 | 87.7 | 3.45 |
| 4 | 5 | 20 | 100 | 83.2 | 4.38 |
| 5 | 5 | 40 | 100 | 82.4 | 8.68 |
| 6 | 3 | 20 | 100 | 78.0 | 6.18 |
| 7 | 2 | 20 | 100 | 74.5 | 7.90 |
| 8 | 2 | 30 | 100 | 73.2 | 11.64 |

EXAMPLE 9

A catalyst was prepared by subjecting bentonite (H) to the same cation exchange treatment as described in Example 1, and the same reaction as in Example 1 was performed in the presence of this catalyst. It was found that the conversion of ethylene oxide was 100%, the selectivity for ethylene glycol monoethyl ether was 91.8%, and the selectivity for diethylene glycol monoethyl ether was 6.1%. Accordingly, the space time yield of ethylene glycol monoethyl ether in this reaction was 2.62 kg/liter of catalyst/hour.

When the above procedure was repeated under the same conditions except that bentonite (H) not treated with the aqueous aluminum chloride, the reaction scarcely proceeded.

EXAMPLES 10 TO 16

Using the catalyst and the reactor described in Example 1, the procedure of Example 1 was performed except that the types of the alcohol and alkylene oxide and the reaction conditions were varied. The results are shown in Table 2.

TABLE 2

| Example | Alcohol | Alkylene oxide | Reaction conditions Mole ratio of the materials | SV | Temperature (°C.) | Conversion of the alkylene oxide (%) | Selectivity (%) for Mono-alkylene product | Di-alkylene product | STY of the monoalkylene product (kg/liter of catalyst/hour) |
|---|---|---|---|---|---|---|---|---|---|
| 10 | Methanol | Ethylene oxide | 10 | 20 | 90 | 100 | 91.8 | 6.0 | 3.07 |
| 11 | i-Propanol | " | 10 | 20 | 90 | 100 | 87.4 | 7.6 | 2.26 |
| 12 | n-Butanol | " | 10 | 20 | 90 | 100 | 85.0 | 9.0 | 2.05 |
| 13 | Ethanol | " | 10 | 20 | 50 | 100 | 90.7 | 6.7 | 2.59 |
| 14 | " | " | 7 | 20 | 90 | 100 | 87.7 | 7.8 | 3.45 |
| 15 | " | Propylene oxide | 10 | 20 | 90 | 100 | 86.2 | 7.3 | 2.77 |
| 16 | " | Butylene | 10 | 20 | 90 | 100 | 83.2 | 9.8 | 2.95 |

EXAMPLES 17 TO 21

The procedure of Example 1 was repeated under the same conditions except that catalysts were prepared by treating the acid clay (A) with an aqueous solution of a salt of 1 meq./g of clay of chromium [Cr(NO$_3$)$_3$], manganese [Mn(NO$_3$)$_2$], iron [Fe(NO$_3$)$_3$], tin (SnCl$_4$) or thorium [Th(NO$_3$)$_4$] instead of the aqueous aluminum chloride solution. The results are shown in Table 3.

TABLE 3

| Example | Exchange ion | Conversion of ethylene oxide (%) | Selectivity (%) for Mono-alkylene product | Di-alkylene product | Space time yield (kg/liter of catalyst/hour) |
|---|---|---|---|---|---|
| 17 | Chromium | 100 | 90.9 | 7.2 | 2.60 |
| 18 | Manganese | 100 | 91.5 | 6.8 | 2.61 |
| 19 | Iron | 100 | 91.4 | 6.7 | 2.61 |
| 20 | Tin | 100 | 87.9 | 9.9 | 2.51 |
| 21 | Thorium | 100 | 92.6 | 5.6 | 2.65 |

COMPARATIVE EXAMPLES 1 TO 8

Colloidal silica as a binder was added in an amount of 20% by weight as SiO$_2$ to each of the acid clays, A, B, C and D and activated clays E, F and G in Comparative Examples 1 to 7. The mixture was molded, dried at 500° C., and calcined for 2 hours.

Using the resulting catalyst, the same reaction as in Example 1 was performed. In Comparative Example 8, a catalyst was used which was obtained by treating the activated clay G with an aqueous solution of aluminum chloride in the same way as in Example 1.

The results are shown in Table 4.

It is seen from the results obtained that acid clays not subjected to cation exchange with a specified metal in accordance with this invention are far inferior to the catalyst of this invention; the activated clay is only slightly better than the acid clay; and that since the montmorillonite structure of acid clay is destroyed during its treatment to produce activated clay, the activated clay cannot produce the effect obtainable by the present invention even after it has been treated with an aqueous solution of a metal salt.

TABLE 4

| Comparative Example | Catalyst | Conversion of ethylene oxide (%) | Selectivity (%) for Mono-alkylene product | Di-alkylene product | STY of the monoalkylene product (kg/liter of catalyst/hour) |
|---|---|---|---|---|---|
| 1 | Acid clay A | 70 | 76.1 | 10.1 | 1.52 |
| 2 | Acid clay B | 63 | 79.5 | 10.0 | 1.43 |
| 3 | Acid clay C | 65 | 78.8 | 10.5 | 1.46 |
| 4 | Acid clay D | 45 | 75.3 | 9.4 | 0.97 |
| 5 | Activated clay E | 86 | 80.4 | 9.8 | 1.98 |
| 6 | Activated clay F | 80 | 82.0 | 8.8 | 1.87 |
| 7 | Activated clay G | 90 | 83.8 | 9.5 | 2.16 |
| 8 | Catalyst | 94 | 83.3 | 9.7 | 2.24 |

TABLE 4-continued

| Comparative Example | Catalyst | Conversion of ethylene oxide (%) | Selectivity (%) for Monoalkylene product | Selectivity (%) for Dialkylene product | STY of the monoalkylene product (kg/liter of catalyst/hour) |
|---|---|---|---|---|---|
| | prepared by treating G with Al solution | | | | |

What is claimed is:

1. In a process for producng a monoalkylene glycol monoether comprising reacting an alkylene oxide having 2 to 4 carbon atoms with an aliphatic alcohol having 1 to 4 carbon atoms to produce the corresponding monoalkylene glycol monoether, the improvement which comprises performing said reaction in the presence of a solid catalyst resulting from the exchanging of exchangeable cations of a clay composed mainly of montmorillonite with at least one cation selected from the group consisting of aluminum, chromium, manganese, iron, tin and thorium.

2. The process of claim 1 wherein said clay is an acid clay or bentonite.

3. The process of claim 1 wherein the reaction temperature is 30° to 200° C.

4. The process of claim 1 wherein the mole ratio of the starting alcohol to the alkylene oxide is from 2 to 20.

5. The process of claim 1 wherein the reaction is carried out by a flowing method using a fixed bed of the catalyst.

6. The process of claim 5 wherein the reaction is carried out at a liquid hourly space velocity of 5 to 70.

* * * * *